United States Patent [19]
Liu et al.

[11] Patent Number: 6,037,588
[45] Date of Patent: Mar. 14, 2000

[54] METHOD FOR TESTING SEMICONDUCTOR DEVICE

[75] Inventors: Guo-Lin Liu; Hidetsugu Uchida; Izumi Aikawa; Naokatsu Ikegami; Norio Hirashita, all of Tokyo, Japan

[73] Assignee: Oki Electric Industry Co., Ltd., Tokyo, Japan

[21] Appl. No.: 09/020,505

[22] Filed: Feb. 9, 1998

[30] Foreign Application Priority Data

Jul. 23, 1997 [JP] Japan .................................. 9-197461

[51] Int. Cl.⁷ .................................................. H01J 37/29
[52] U.S. Cl. ............................................ 250/307; 250/309
[58] Field of Search .................................. 250/307, 309, 250/492.21

[56] References Cited

U.S. PATENT DOCUMENTS

| | | | |
|---|---|---|---|
| 4,132,892 | 1/1979 | Wittmaack | 250/309 |
| 4,611,120 | 9/1986 | Bancroft et al. | 250/309 |
| 4,661,702 | 4/1987 | Welkie | 250/309 |
| 4,748,325 | 5/1988 | Slodzian | 250/309 |
| 4,874,946 | 10/1989 | Kazmerski | 250/309 |
| 4,874,947 | 10/1989 | Ward et al. | 250/309 |
| 4,992,661 | 2/1991 | Tamura et al. | 250/309 |
| 5,336,895 | 8/1994 | Nakano | 250/309 |
| 5,442,174 | 8/1995 | Kataoka et al. | 250/309 |
| 5,521,377 | 5/1996 | Kataoka et al. | 250/309 |

FOREIGN PATENT DOCUMENTS

| | | |
|---|---|---|
| 4-239146 | 8/1992 | Japan . |
| 4-273143 | 9/1992 | Japan . |
| 8-298275 | 11/1996 | Japan . |

OTHER PUBLICATIONS

Guo-Lin Liu et al., "Micro-analysis of Submicron Via Holes by Using AES," The Institute of Electronics, Information and Communication Engineers, Technical Report of IEICE, pp. 47–52, (Abstract in English).

*Primary Examiner*—Bruce C. Anderson
*Attorney, Agent, or Firm*—Jones Volentine, L.L.P.

[57] ABSTRACT

In order to achieve a method for analyzing the compositional distribution of deposited film adhering to the internal surface of a contact hole having a diameter in the deep submicron order, primary ions 18 are radiated into the surface 12a of an insulating film 12 where the contact hole 14 is formed to generate secondary ions 20. The primary ions are radiated into the surface of the insulating film from a constant diagonal direction. Then, mass spectrometry is performed on the resulting secondary ions to detect the compositional distribution of the deposited film 16 formed at the internal surface of the contact hole. Thus, the compositional distribution of the deposited film is ascertained over the depthwise direction of the contact hole.

20 Claims, 10 Drawing Sheets

METHOD FOR TESTING SEMICONDUCTOR DEVICE

BACKGROUND OF THE INVENTION

The present invention relates to a method for characterizing the compositional distribution at the internal surface of a contact hole in the direction of its depth after the contact hole is formed to contribute to establishing a contact hole formation process in the method for manufacturing semiconductor integrated circuits.

With higher integration in large-scale semiconductor integrated circuit (hereafter referred to as LSI) devices increasingly called for in recent years, the number of circuit elements is rising. This has resulted in an increase in the number of contact holes required for forming wiring, and the diameter of these contact holes is steadily being reduced. Because of this, formation of contact holes is becoming ever more difficult. Contact holes are formed through etching. On the internal surface of a contact hole formed through etching, a deposited film is formed with an etching gas or the like. This deposited film is basically constituted of the accumulated residue from the etching process. In order to establish a method for forming contact holes, it is necessary to optimize the etching process by examining the compositional distribution of the deposited film.

A method in the prior art for determining the compositional distribution at the internal surface of a hole is disclosed in a publication entitled "Electronics Information Communication Society Technical Report," Vol. 93, No.369, pp.47–52. In the method disclosed in this publication, the internal surface of a through hole is exposed by cutting open a multilayer wiring test piece. Then, by employing Auger electron spectroscopy, the deposited film formed at the internal surface of the through hole is analyzed.

However, no method for analyzing the compositional distribution at the internal surface of a contact hole with a diameter in the deep submicron range, or several tens of nanometers (nm), and a depth of 1 micrometer or more has been disclosed to date. Thus, optimization of the etching process for contact holes has not been achieved, and it has been difficult to form contact holes with an aspect ratio of, for instance, 20:1.

OBJECTS AND SUMMARY OF THE INVENTION

Accordingly, an object of the present invention is the realization of a method for analyzing the compositional distribution of a deposited film adhering to the internal surface of a contact hole with a diameter in the deep submicron range.

The inventors of the present invention have conducted focused research and have learned that the compositional distribution at the internal surface (side wall) of a contact hole can be analyzed by employing SIMS (secondary ion mass spectrometry).

The method for detecting the compositional distribution at the hole internal surface according to the present invention is characterized in that; secondary ions are generated by radiating primary ions from a constant oblique direction into the surface of a test insulating film where a contact hole is formed; in that mass spectrometry is performed on the secondary ions to detect the depth-wise compositional distribution of the test insulating film; in that the formation of the contact hole is verified by comparing the depth-wise compositional distribution thus ascertained with the depth-wise compositional distribution of a reference insulating film that has been measured in advance; and in that the depth-wise compositional distribution of the test insulating film is determined to be the depth-wise compositional distribution of foreign matter adhering to the internal surface of the contact hole.

Namely, the surface of the test insulating film where the contact hole is formed is irradiated with primary ions. It is desirable to radiate the primary ions from a constant oblique direction relative to the surface of the test insulating film, since this will cause the primary ions to readily enter the internal surface of the contact hole. When the angle of incidence of the primary ions relative to the surface of the insulating film is represented by theta and the diameter of the contact hole is represented by phi, for instance, the area of the hole internal surface over the distance expressed as phi×tan theta along the depth-wise direction from the surface of the test insulating film is irradiated with the primary ions.

When the primary ions are irradiated, foreign matter adhering to the surface of the insulating film and the hole internal surface, i.e., the substances constituting the surface of the deposited film, become sputtered and secondary ions and the like are generated. Then, by performing mass separation on the resulting secondary ions, the quantity of specific secondary ions can be detected. As a result, the compositional ratio of the elements constituting the deposited film is determined.

In addition, since the surface of the insulating film is sputtered using primary ions, the surface is gradually eroded. Consequently, the length of the internal surface of the contact hole along its depth-wise direction can be gradually irradiated with the primary ions. This makes it possible to perform gradual scanning of the internal surface of the contact hole along the depth-wise direction using the primary ions, to ultimately determine the compositional distribution of the deposited film over the depth-wise direction of the contact hole.

Moreover, by comparing the depth-wise compositional distribution thus ascertained with the depth-wise compositional distribution of a reference insulating film that has been measured in advance, the formation of the contact hole in the test insulating film is verified.

Thus, the compositional distribution over the depth-wise direction of the deposited film accumulated at the internal surface of the contact hole can be ascertained. This information is expected to contribute to resolving the unknown aspects of various phenomena that take place during the etching process and, ultimately, is expected to contribute to realizing the optimization of the etching conditions for forming contact holes such as the composition of the etching gas and the various settings of the etching apparatus. Consequently, the method according to the present invention is effective when adopted in the formation of contact holes with smaller diameter and greater depth.

In addition, with the method according to the present invention, it is not necessary to cut open the test piece as in the prior art. As a result, the test can be performed faster and more easily compared to the method in the prior art.

Moreover, in the method for detecting the compositional distribution at the hole internal surface according to the present invention, it is desirable to fill the inside of the contact hole with the same material as that constituting the test insulating film.

This will eliminate the phi×tan theta misalignment mentioned above relative to the surface of the insulating film and, as a result, the depth-wise position at the hole internal surface where the primary ions are radiated at a given point in time and the height-wise position at the surface of the insulating film at the same point in time will match. Thus, the depth in the compositional distribution of the deposited film can be determined accurately.

In another aspect, the method for detecting the compositional distribution at the hole internal surface according to the present invention is characterized in that; at least one marker layer is provided in advance at a specific depth-wise position relative to the surface of an insulating film where a contact hole is formed; in that secondary ions are generated by radiating primary ions into the surface of the insulating film from a constant diagonal direction; in that the depth-wise compositional distribution of foreign matter adhering to the internal surface of the contact hole is detected by performing secondary ion mass spectrometry; and in that the depth-wise compositional distribution thus detected is calibrated based upon the depth of the marker layer.

By constituting the test piece in this manner it becomes possible to detect the elements constituting the marker layer as well as detecting the compositional distribution of the deposited film. Since this marker layer is provided at a specific depth-wise position in the insulating film, the depth-wise calibration of the compositional distribution of the deposited film can be implemented.

Moreover, when implementing the method for detecting the compositional distribution at the hole internal surface according to the present invention, it is ideal to provide a first marker layer at the bottom surface of the insulating film, to provide a second marker layer at an intermediate position of the insulating film and to provide a third marker layer at the upper surface of the insulating film.

In addition, the method for testing a semiconductor device according to the present invention through which a semiconductor is tested to determine whether or not contact holes have been properly formed in an insulating film, is characterized in that; secondary ions are generated by radiating primary ions into the surface of the insulating film where a contact hole is formed from a constant diagonal direction; in that the depth-wise compositional distribution of the insulating film is determined by performing mass spectrometry on the secondary ions; and in that decision making as to whether or not a contact hole is properly formed is performed by comparing the depth-wise compositional distribution thus ascertained and the depth-wise compositional distribution of a reference insulating film that has been measured in advance.

For instance, a contact hole may be formed in an insulating film formed at the upper surface of a substrate. When a contact hole is formed through etching, the etching stops at the upper surface of the substrate, which results in a relatively thick deposited film being formed at the bottom of the contact hole. Since the film thickness of the deposited film accumulated at the bottom is greater than the film thickness in other areas, it is possible to detect the position of the bottom of the contact hole by ascertaining the compositional distribution through the method for detecting the compositional distribution at the hole internal surface described earlier. Consequently, it is possible to make a decision as to whether or not the contact hole is fully open, i.e., whether or not the etching has reached the upper surface of the substrate.

BRIEF DESCRIPTION OF THE DRAWINGS

The above and other features of the invention and the concomitant advantages will be better understood and appreciated by persons skilled in the field to which the invention pertains in view of the following description given in conjunction with the accompanying drawings which illustrate preferred embodiments. In the drawings.

DETAILED DESCRIPTION OF THE PREFERRED EMBODIMENTS

The following is an explanation of preferred embodiments of the invention in reference to the drawings. It is to be noted that, to facilitate understanding of the present invention, the drawings only present schematic illustrations of the structures, sizes and positional relationships. In addition, the conditions, including numerical values, and the materials mentioned in the following explanation are only given as examples. Therefore, the present invention is not limited to these embodiments in any way whatsoever.

First embodiment

Figure 1:
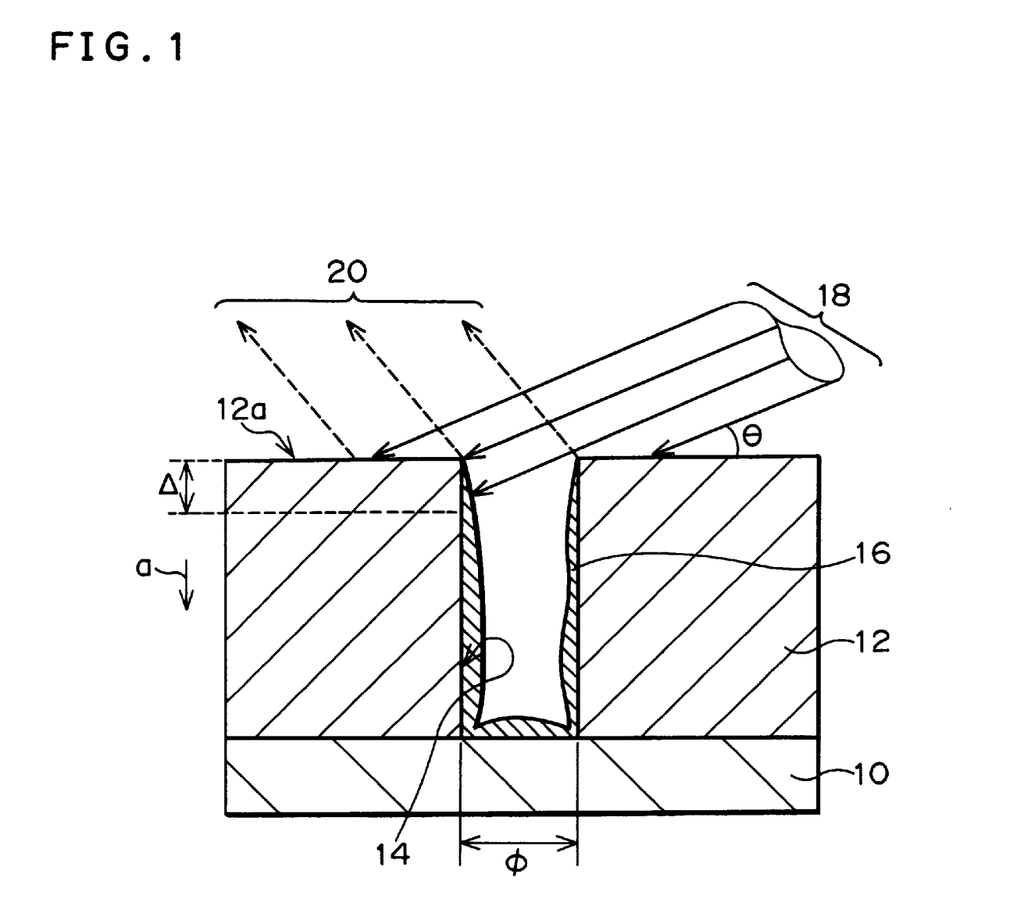
FIG. 1 illustrates the method for detecting the compositional distribution.

The method for detecting the compositional distribution at the hole internal surface in this embodiment is explained in reference to FIG. 1, which illustrates the method for detecting the compositional distribution, showing the cross section of an area that contains a contact hole 14.

In this embodiment, a contact hole 14 is formed in an insulating film 12 which is formed at the upper surface of a silicon substrate 10. The insulating film 12 to be used for testing, may be constituted of, for instance, a BPSG (silicate glass containing boron (B) and phosphorus (P)) film. The contact hole 14 may be formed through, for instance, magnetron plasma etching. A CF gas, for example, CHF3 gas, that contains carbon (C) and fluorine (F) is used as the etching gas.

Now, the etching process is briefly explained. When high frequency power is applied with an etching gas induced into a vacuum, plasma is generated which, in turn, generates ions and radicals. The positive ions thus generated become accelerated by the internal electric field and collide with the surface of the insulating film 12. With this collision, an altered layer (defective layer) is formed at the surface of the insulating film 12. This altered layer readily reacts with the radicals. Thus, the radicals react with the altered layer, forming a volatile gas as a reaction product. As a result, the surface portion of the insulating film 12 is eroded. Since Sthe impact is applied to the surface of the insulating film 12 from almost the same direction at all times, the process of anisotropic etching progresses.

It is to be noted that while the etching is in progress, a deposited film is accumulated at the side wall formed through the etching. This deposited film is mainly constituted of adhered residue (foreign matter) formed during the etching process. If a CF etching gas is employed, as in this case, a polymer film constituted of C and F, i.e., a fluorocarbon polymer film, is formed as the deposited film. Since side etching is inhibited by the deposited film, the anisotropic tendency is intensified. Ascertaining the compositional distribution of the deposited film is crucial for optimizing the etching conditions, such as the mixing ratio of the etching gas, the etching time and the substrate temperature.

In this embodiment, SIMS (secondary ion mass spectrometry) is adopted to determine the compositional distribution of the deposited film. Namely, by radiating primary ions 18 into the surface 12a of the insulating film 12 where the contact hole 14 is formed, secondary ions 20 are generated and by performing mass spectrometry on the secondary ions 20, the compositional distribution of the deposited film 16 formed at the internal surface of the contact hole 14 is detected. Through this method, the composition of the deposited film 16 can be ascertained over the depth-wise direction of the contact hole 14.

First, as in normal SIMS, the primary ions 18 are radiated into the surface 12a of the insulating film 12 from a constant diagonal direction in the form of a beam. The optimal angle of incidence theta of the primary ions 18 relative to the surface 12a of the insulating film 12 is within the range of 7 degrees to 70 degrees. In normal SIMS, the angle of incidence is often set at approximately 30 degrees. For the reason that is to be detailed below, a higher degree of detection accuracy is achieved with a smaller angle of incidence theta. However, a small angle of incidence theta will reduce the area of the deposited film 16 that is irradiated with the primary ions 18, resulting in reduced detection sensitivity. Therefore, the angle of incidence theta must be set by taking into consideration the necessity for achieving the best balance between accuracy and sensitivity requirements.

The primary ions 18 may be, for instance, oxygen ions. As explained above, the primary ions 18 are radiated into the surface 12a of the insulating film 12 from a diagonal direction. Thus, the primary ions 18 are radiated into the internal surface of the contact hole 14 in the vicinity of the surface 12a of the insulating film 12 and into the surface 12a of the insulating film. This means that a portion of the surface of the deposited film 16 is irradiated with the primary ions 18.

When the diameter of the contact hole 14 is represented by phi, the deepest point of entry of the primary ions 18 is the position that is below the surface 12a of the insulating film 12 by a distance delta=phi×tan theta in the depth-wise direction. Consequently, the primary ions 18 are radiated into the side wall surface over the range of the distance delta. The surface 12a of the insulating film 12 is sputtered by the primary ions 18 and is eroded, generating the secondary ions 20. As a result, as time elapses, the height of the surface 12a becomes gradually reduced. As the height of the surface 12a becomes reduced, the irradiation area of the primary ions 18 moves downward along the depth-wise direction (the direction indicated by the arrow "a" in FIG. 1) of the contact hole 14. Thus, the surface of the deposited film 16 formed at the internal surface of the contact hole 14 can be scanned with the primary ions 18 over the depth-wise direction of the hole.

Figure 2A:
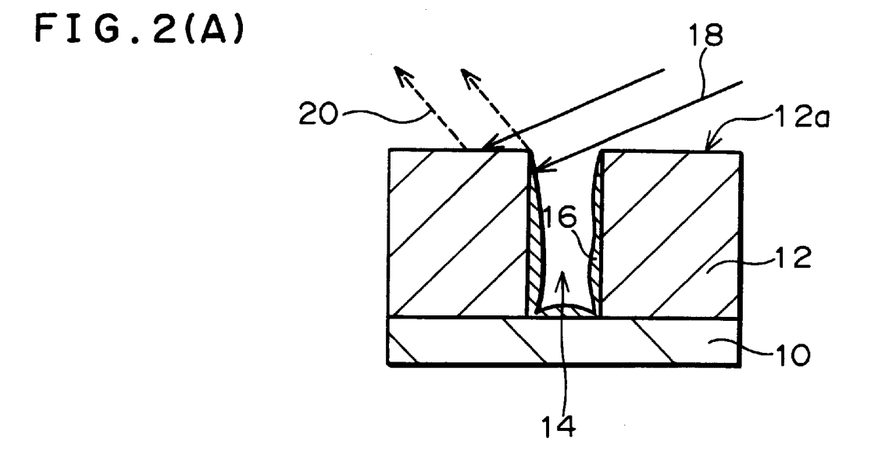
FIG. 2 illustrates compositional analysis through SIMS.
Figure 2B:
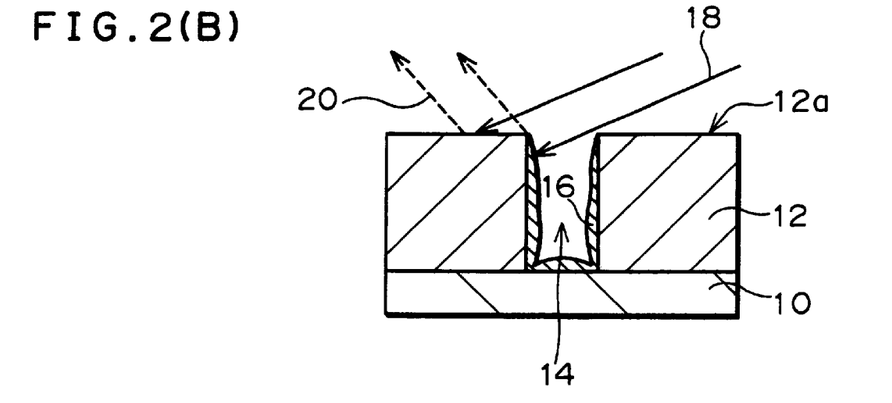
Figure 2C:
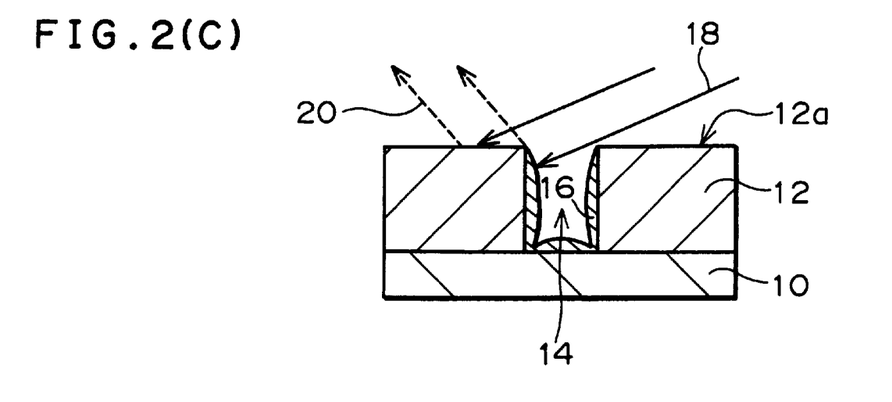

FIG. 2 illustrates the compositional analysis performed by employing SIMS. FIGS. 2(A), 2(B) and 2(C) respectively show a cross section of the test piece shown in FIG. 1 at various positions of radiation. As time elapses, the structure of the test piece sequentially changes as illustrated in FIGS. 2(A), 2(B) and 2(C). In other words, by radiating the primary ions 18, the height of the surface 12a of the insulating film 12 becomes gradually reduced. Consequently, the position at which the deposited film 16 is irradiated with the primary ions 18 is gradually lowered, thereby generating the secondary ions 20 along the internal surface of the contact hole 14.

It is to be noted that at an initial point in time at which the irradiation with the primary ions 18 is started, the area of the deposited film 16 over the range of the distance delta is irradiated at once. As a result, at this point, an averaged composition in the area over the distance delta is detected, and detection is not performed for the distribution in the depth-wise direction. However, at positions deeper than the distance delta, the compositional distribution (profile) over the depth-wise direction is detected with a high resolution, corresponding to the resolution of SIMS.

In addition, when, for instance, the diameter phi of the contact hole 14 is set at 0.06 micrometers and the angle of incidence theta of the primary ions 18 is set at 7 degrees, the value for delta is approximately 7 nm because of the relationship expressed as delta=phi×tan theta. Since the depth of the contact hole 14 which is to be analyzed may be, for instance, approximately 5 micrometers, such a value for delta can be disregarded.

As has been explained, the smaller the distance delta, the higher the degree of accuracy that can be achieved in analysis. Since the distance delta is expressed as phi×tan theta, the value of delta becomes smaller when the angle of incidence theta is set at a smaller value. Consequently, as explained above, the accuracy of detection improves when the angle of incidence theta is set small to make it possible to ascertain the true compositional distribution.

Figure 3A:
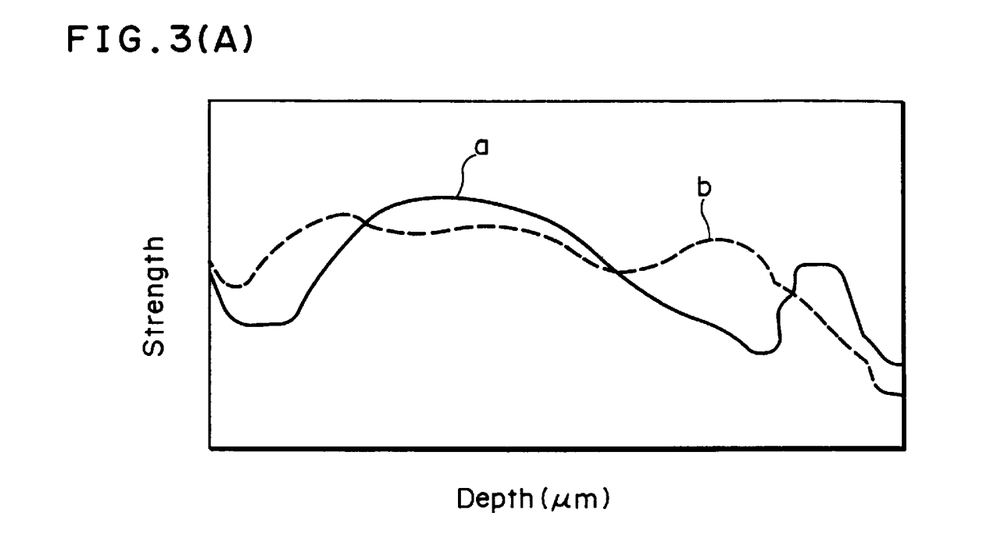
FIG. 3 shows the C and F profiles obtained through SIMS.

FIG. 3 is a graph of the C and F profiles obtained through SIMS. FIG. 3(A) schematically presents the results of detection of the compositional distribution of the deposited film 16 obtained through the analysis method explained in reference to FIGS. 1 and 2. The horizontal axis of the graph in the figure represents the depth (in units of micrometers) relative to the initial surface 12a of the insulating film 12. The vertical axis in the graph in the figure represents the strength of the secondary ion 20 reading, i.e., the quantity of C ions or F ions detected. The depth relative to the surface 12a may be determined based upon the sputtering rate, and may be detected as a quantity that is in proportion to the length of time over which the primary ions 18 are radiated.

Figure 3B:
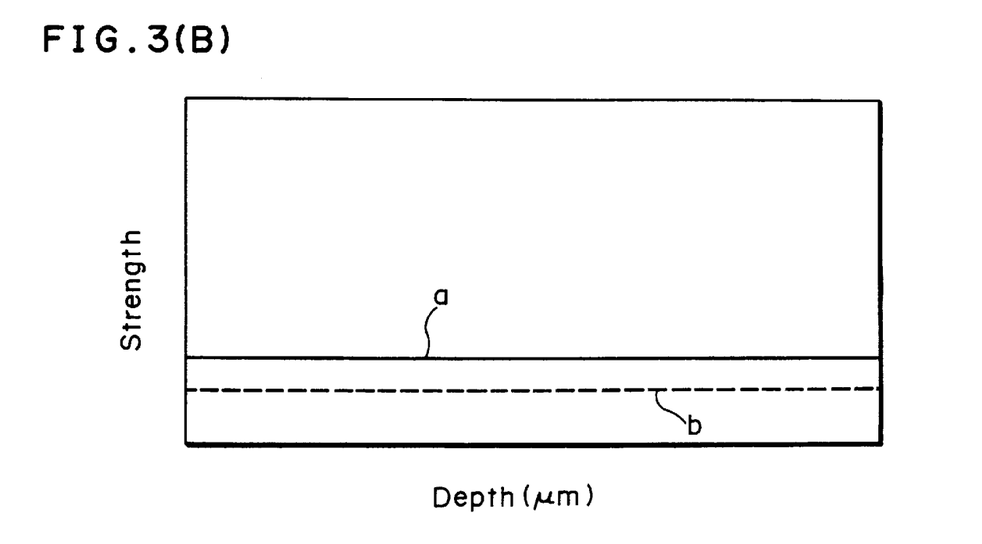

In addition, FIG. 3(B) shows the depth-wise compositional distribution of a reference insulating film. The reference insulating film is constituted of the same material as that constituting the insulating film 12. However, no contact hole is formed in it. The depth-wise compositional distribution of this reference insulating film is ascertained by adopting the analysis method explained in reference to FIGS. 1 and 2. By comparing the depth-wise compositional distribution of the reference insulating film and the compositional distribution ascertained for the insulating film 12, the formation of the contact hole 14 in the insulating film 12 is confirmed.

When the primary ions 18 are radiated as described above, the atoms such as C, F, Cl and H that constitute the deposited film 16 and ions are generated together with Si and O that constitute the insulating film 12. The ions thus generated (secondary ions 20) are accelerated by the electric field and are each turned in a direction corresponding to its mass by the magnetic field. Then, with a detection device installed at a specific position, the ionic strength of each mass is detected so that the composition of the deposited film 16 can be ascertained. In addition, the position at which the primary ions 18 enter the deposited film 16 gradually moves downward along the depth-wise direction of the contact hole 14 so that the depth-wise compositional distribution of the deposited film 16 can be ascertained. For instance, the curve "a" in FIG. 3(A) represents the compositional distribution of C, which is one of the constituents of the deposited film 16. In addition, the curve "b" in FIG. 3(A) represents the compositional distribution of F which is another constituent of the deposited film 16. As FIG. 3(A) indicates, the ionic intensities of the C and F secondary ions are not constant relative to the depth.

The curve "a" in FIG. 3(B) represents the compositional distribution of C and the curve "b" in FIG. 3(B) represents the compositional distribution of F. As the figure indicates, in the case of the reference insulating film, in which no contact holes are formed, the ionic intensities of the C and F secondary ions, which are the constituents of the deposited film 16, are practically constant relative to the depth. These ionic strengths of the secondary ions correspond to the background of the respective compositional distributions shown in FIG. 3(A). Thus, by comparing the compositional distributions in FIG. 3(A) and the compositional distributions in FIG. 3(B), the formation of the contact hole 14 in the insulating film 12 can be verified. In addition, the compositional distribution in FIG. 3(A) is verified to be a depth-wise distribution of the elements constituting the deposited film 16 formed at the internal surface of the contact hole 14.

As has been explained, by employing SIMS, the compositional distribution of the deposited film 16 formed at the internal surface of the contact 14 hole over its depth-wise direction can be analyzed. Although there may be a concern that since the primary ions 18 are used to perform sputtering to generate the secondary ions 20 in SIMS, the desired results may not be achieved due to a compacted contact hole 14, the testing conducted by the inventors has confirmed that the contact hole 14 does not become compacted and that the surface 12a of the insulating film 12 is gradually eroded.

Thus, by employing SIMS, the compositional distribution of the deposited film formed at a contact hole of a relatively small size can be detected with a high degree of accuracy. For instance, the compositional distribution of a deposited film formed at a contact hole with a diameter of approximately 0.05 micrometers to 0.5 micrometers can be analyzed. Previously, it has not been possible to analyze the compositional distribution of a deposited film at a contact hole in this size range. According to the present invention, by adopting SIMS, the compositional distribution of a deposited film at a contact hole of a relatively small size can be analyzed as explained above. As a result, optimization of the etching process can be achieved to enable formation of contact holes of a smaller size.

Second embodiment

Figure 4A:
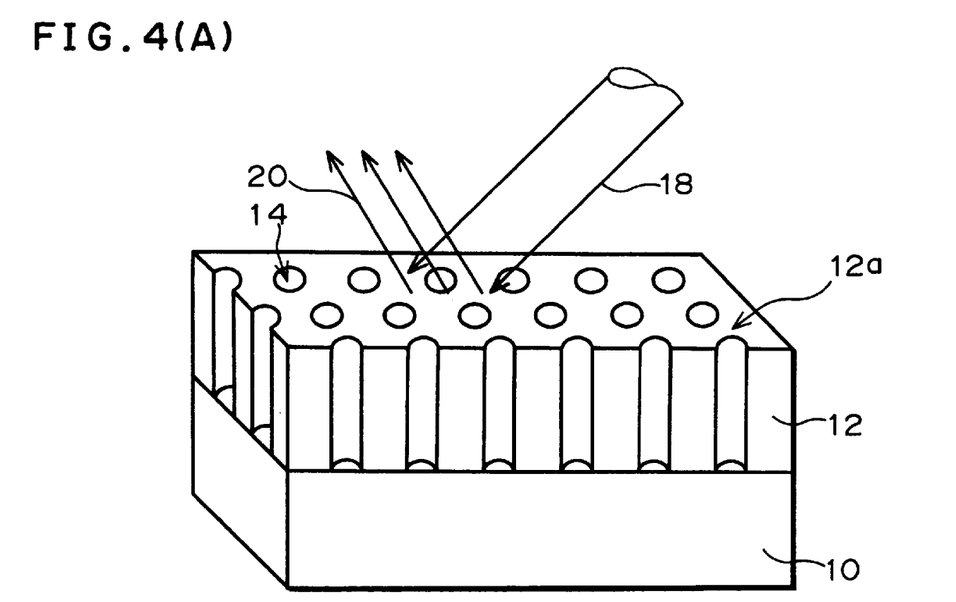
FIG. 4 shows the structure of a test piece for compositional distribution detection.
Figure 4B:
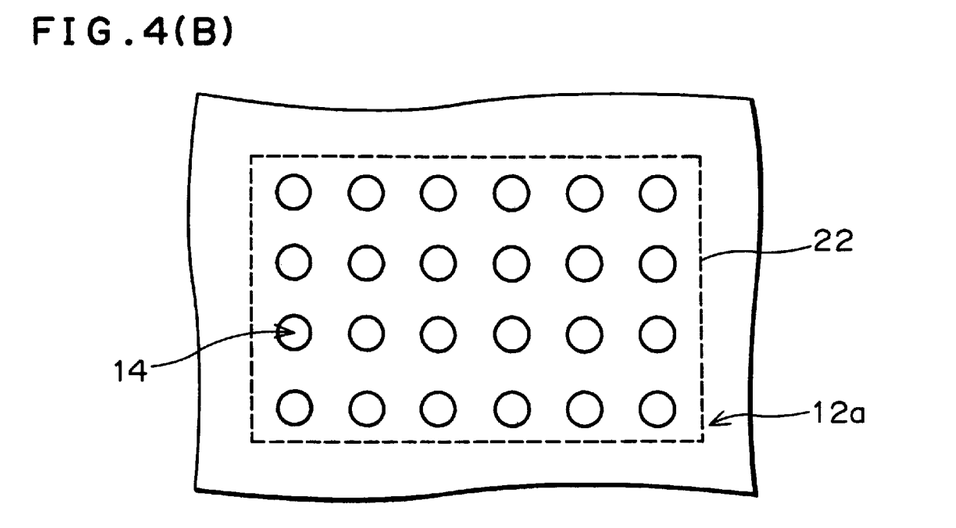

Next, a second embodiment of the present invention is explained in reference to FIG. 4, which illustrates the structure of a test piece for compositional distribution detection. FIG. 4(A) is a perspective of the essential portion of a cut off test area 22 showing the structure of the test piece. It is to be noted that the hatching of the cross sectional surface is omitted. FIG. 4(B) is a plan view of the essential portion illustrating the surface 12a of the insulating film 12 constituting the test piece structure. It is to be noted that in FIG. 4, the deposited film is not illustrated. In addition, repeated explanation of features identical to those in the first embodiment may be omitted.

In the second embodiment, the test area 22 is defined at the surface 12a of the insulating film 12, with a plurality of contact holes 14 formed within the test area 22. Then, the test area 22 is scanned with the primary ions 18.

The structure of the test piece shown in FIG. 4 is achieved by forming an insulating film 12 such as BPSG at the upper surface of a silicon substrate 10. The test area 22 is defined at the surface 12a of the insulating film 12. The test area 22 shown in FIG. 4(B) may be, for instance, a quadrangular area with the length of each side at approximately 100 micrometers. Within this test area 22, 1000 or more contact holes 14, for instance, with the same diameter are formed.

As shown in FIG. 4(A), the primary ions 18 are radiated into a portion within the test area 22 in the form of a beam. The irradiated area where the radiation is performed with the primary ions 18 moves with a specific regularity within the test area 22. Thus, an area of the surface 12a of the insulating film 12 included within the test area 22 are scanned with the primary ions 18. Ideally, this scanning should be performed employing the raster method.

As explained above, with a test piece structure having a plurality of contact holes 14, it is necessary to radiate the primary ions 18 over a relatively large area. However, by performing the scanning with a specific regularity as described above, the compositional distribution of the deposited film can be detected over the depth-wise direction of the contact holes 14 as has been explained in reference to the first embodiment.

The method described above achieves an advantage in that a great number of contact holes can be analyzed at practically the same time. As a result, since the quantity of the deposited film that can be analyzed increases and the strengths of the secondary ions 20 that are detected also become relatively large, the compositional distribution is detected with an even higher degree of sensitivity. This, in turn, is expected to contribute to the resolution of various unknown aspects of the phenomena occurring during the etching process even more clearly.

Third embodiment

Figure 5:
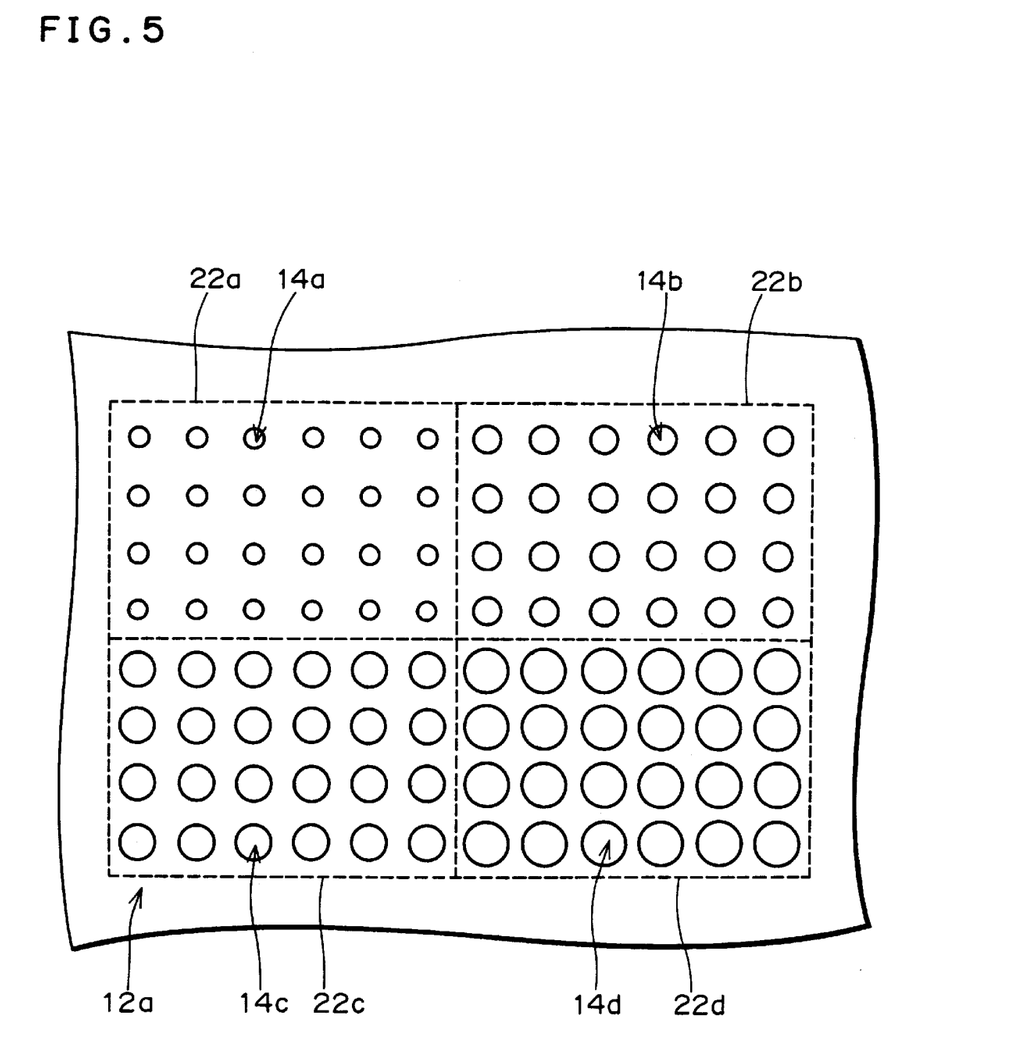
FIG. 5 shows the structure of a test piece having a plurality of test areas.

Now, the third embodiment of the present invention is explained in reference to FIG. 5, which presents a plan view of a test piece structure having a plurality of test areas.

In the third embodiment, at least two test areas are defined at the surface 12a of the insulating film 12. At the surface 12a in FIG. 5, four test areas 22a, 22b, 22c and 22d are defined. In addition, a plurality of contact holes 14a, 14b, 14c and 14d are formed respectively in the individual test areas 22a to 22d. Furthermore, the diameters of the contact holes 14a to 14d in the individual test areas 22a to 22d differ.

In this test piece structure, the test areas 22a to 22d are formed as identical quadrangular areas of equal size. Each of the test areas 22a to 22d may be, for instance, a quadrangular area having an area of 100 micrometers×100 micrometers. One thousand or more contact holes, for instance, are formed in each of the test areas 22a to 22d.

As explained above, in the test areas 22a, 22b, 22c and 22d, a plurality of contact holes 14a, 14b, 14c and 14d respectively are formed. Test piece structure is designed so that the diameters of the contact holes increase in the order of 14a, 14b, 14c and 14d. Thus, test areas having contact holes with varying diameters are formed on one test piece.

When analyzing this test piece structure, scanning with primary ions is performed as has been explained in reference to the second embodiment, on each of the test areas 22a to 22d. By doing so, the compositional distribution of the deposited film formed at the internal surfaces of the individual contact holes 14a to 14d can be ascertained. Therefore, the dependency of the etching conditions upon the diameter of the contact holes can be determined.

Furthermore, as has been explained in reference to the second embodiment, since a great number of contact holes are analyzed at the same time, detection can be achieved at a high degree of sensitivity.

Fourth embodiment

Now, the fourth embodiment of the present invention is explained. In the test piece structure in this embodiment, a film constituted of elements that do not affect the detection of the compositional distribution is used to constitute the insulating film. For instance, if the compositional ratio of C and F is to be detected, contact holes are formed in an insulating film that does not contain C or F.

Figure 6:
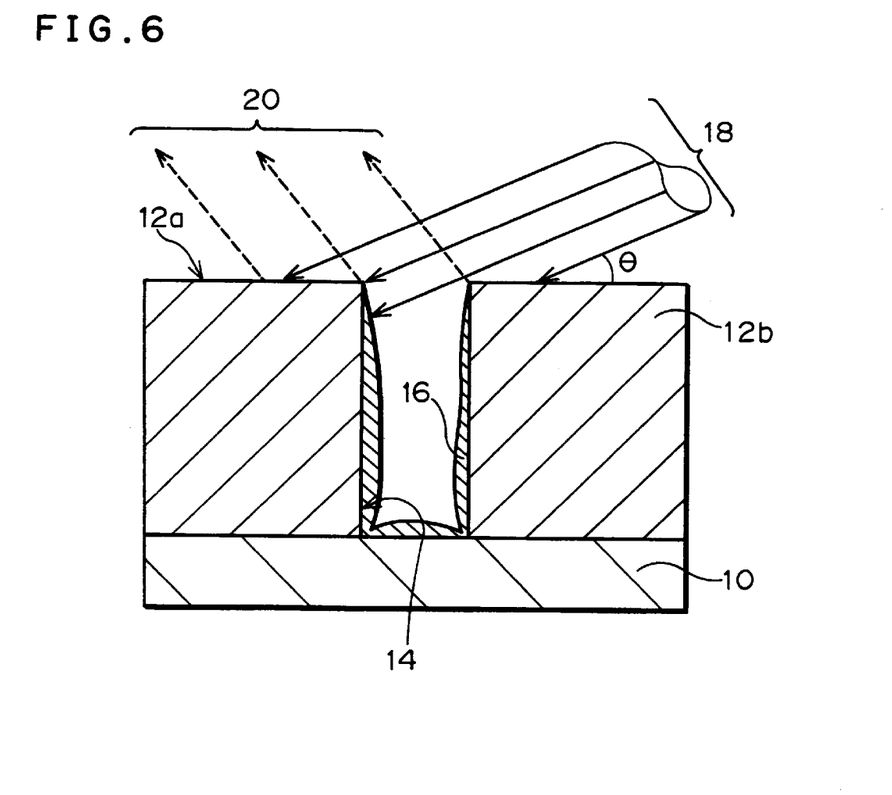
FIG. 6 shows the structure of a test piece having an insulating film that does not contain B, F, C or H.

FIG. 6 illustrates a test piece structure in which an insulating film 12b that does not contain B, F, G or H is formed. FIG. 6 is a cross sectional view of a cut-off edge that includes a contact hole 14. The insulating film 12b is formed at the upper surface of the silicon substrate 10. The contact hole 14 is formed in this insulating film 12b. As has been explained in reference to the first embodiment, primary ions 18 are radiated into the surface 12a of the insulating film 12b from a constant diagonal direction (angle of incidence theta). Then, by performing mass spectrometry on the resulting secondary ions 20, the compositional distribution of the deposited film 16 formed at the internal surface of the contact hole 14 is analyzed.

As explained earlier, when the primary ions 18 enter the surface 12a of the insulating film 12b and the surface of the deposited film 16, these films are sputtered, thereby generating secondary ions 20. Thus, if the insulating film 12b contains C, F and H that are atoms constituting the deposited film 16, the ionic strength of the secondary ions generated from the insulating film 12b are added onto the profile of the deposited film as background, thereby preventing the true compositional distribution in the deposited film 16 from being ascertained. However, in this embodiment, since the contact hole 14 is formed in the insulating film 12b described above, the compositional distribution of C and F in the deposited film 16, for instance, can be measured accurately.

In addition, if the insulating film contains B and H as impurities, $^{11}B\ ^{1}H^{+}$ ions are generated. Since the $^{11}B\ ^{1}H^{+}$ ions have the same mass as the $C^{+}$ ions, they were difficult to be distinguished from each other in mass spectrometry. However, since the insulating film 12b described above does not contain B or H, this addition of background does not occur.

In this embodiment, as the insulating film 12b not containing B, F, C or H, an NSG film (silicate glass that does not contain any impurities) or a SiO2 film formed through CVD, for instance, may be used.

Figure 7:
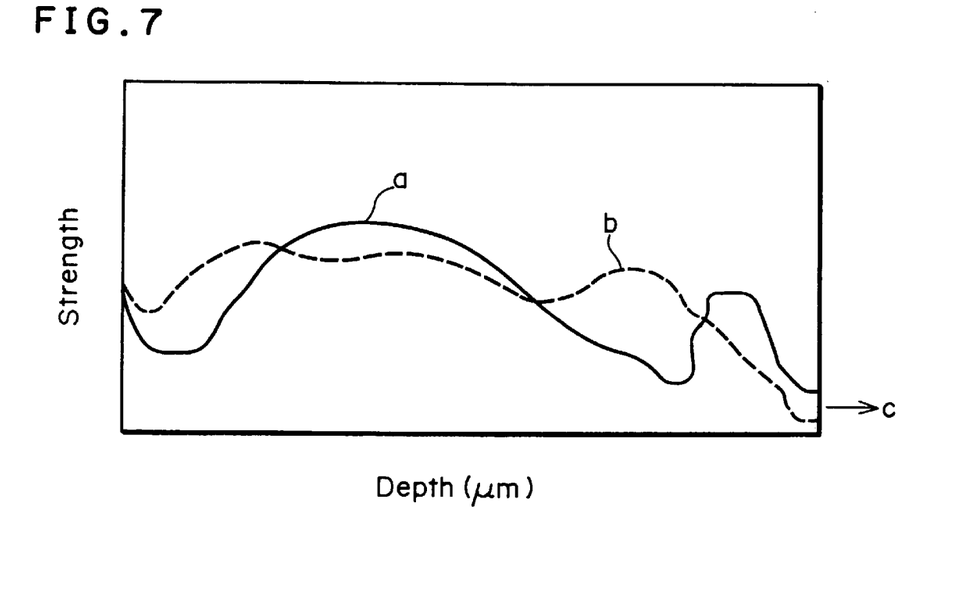
FIG. 7 shows a profile that does not include B, F, C or H.

FIG. 7 presents a graph showing the C and F profiles obtained when the contact hole 14 is formed in the insulating film 12b that does not contain B, F, C or H. The horizontal axis of the graph in FIG. 7 represents the depth of the contact hole 14 (in units of micrometers), whereas the vertical axis of the graph in FIG. 7 represents the strength of the detected secondary ions. The curve "a" in the graph represents the profile of C and the curve "b" represents the profile of F. In order to demonstrate the advantages achieved by using a different insulating film, the profiles are presented in the same format as the profiles in FIG. 3. The position indicated by the arrow "c" in FIG. 7 is the height of the background. In comparison to the profiles in FIG. 3, the background is lowered.

As has been explained, in this embodiment, since the contact hole 14 is formed in the insulating film 12b that does not contain B, F, C or H, the adverse effect of these impurities is eliminated. Thus, we can expect the compositional distribution to be measured with a higher degree of sensitivity.

Fifth embodiment

Figure 8:
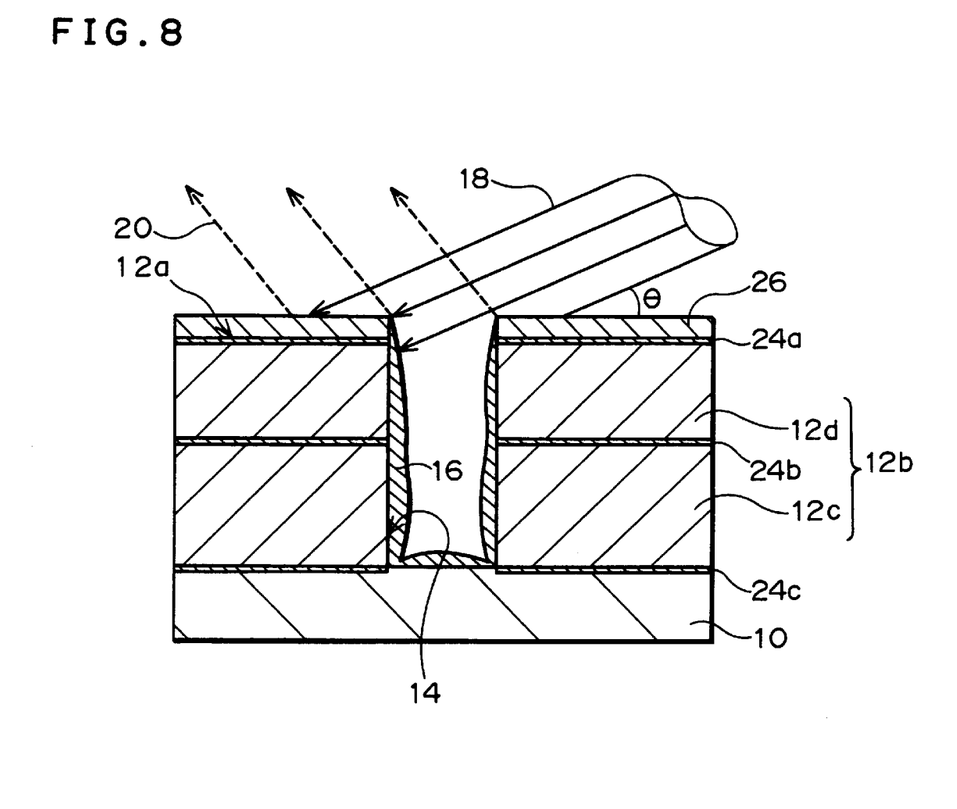
FIG. 8 shows the structure of a test piece with marker layers.

Now, the fifth embodiment of the present invention is explained. In this embodiment, at least one marker layer is formed in the insulating film 12b to be used for the calibration of the depth in the compositional distribution. FIG. 8 illustrates the structure of a test piece in which the marker layers are formed. FIG. 8 presents a cross section at a cut-off edge that includes a contact hole 14.

The insulating film 12b in FIG. 8 is an insulating film that does not contain B or F, and may be constituted of, for instance, NSG. The insulating film 12b is formed at the upper surface of the silicon substrate 10. In this embodiment, the insulating film 12b is constituted by laminating a first insulating film 12c and a second insulating film 12d in that order. Three marker layers 24a, 24b and 24c are formed in the insulating film 12b.

The marker layer 24c is formed at the upper surface of the silicon substrate 10 and the first insulating film 12c is formed on top of this marker layer 24c. The marker layer 24b is formed on top of the first insulating film 12c and the second insulating film 12d is formed on top of the marker layer 24b. Then the marker layer 24a is formed on top of the second insulating film 12d and an etching mask 26 is formed on top of the marker layer 24a. The etching mask 26 may be constituted of, for instance, polysilicon. Etching is performed using the etching mask 26 to form the contact hole 14. Through this etching, the deposited film 16 to be analyzed is formed at the internal surface of the contact hole 14.

The marker layers 24a to 24c are constituted of impurity layers whose elements do not affect the detection of the compositional distribution. When NSG is used to constitute the insulating film 12b, the marker layers 24a to 24c may be constituted of, for instance, P or As. Since these elements are not contained in the deposited film 16, they do not affect the detection of C and F that constitute the deposited film 16.

In addition, the marker layers 24a to 24c are formed through, for instance, normal ion implantation. In the process of ion implantation, the energy for implantation should be set at a relatively low level to ensure that ions are implanted into the superficial portion of the silicon substrate 10, the first insulating film 12c and the second insulating film 12d. Alternatively, the marker layers 24a–24c may be formed by intentionally contaminating the surfaces of the silicon substrate 10, the first insulating film 12c and the second insulating film 12d by exposing them to the atmosphere.

Analysis of the composition is performed on the test piece structure explained above by employing SIMS. For this purpose, the primary ions 18 are radiated into the surface 12a of the insulating film 12b from a constant diagonal direction (angle of incidence theta), and mass spectrometry is performed on the resulting secondary ions 20.

Figure 9:
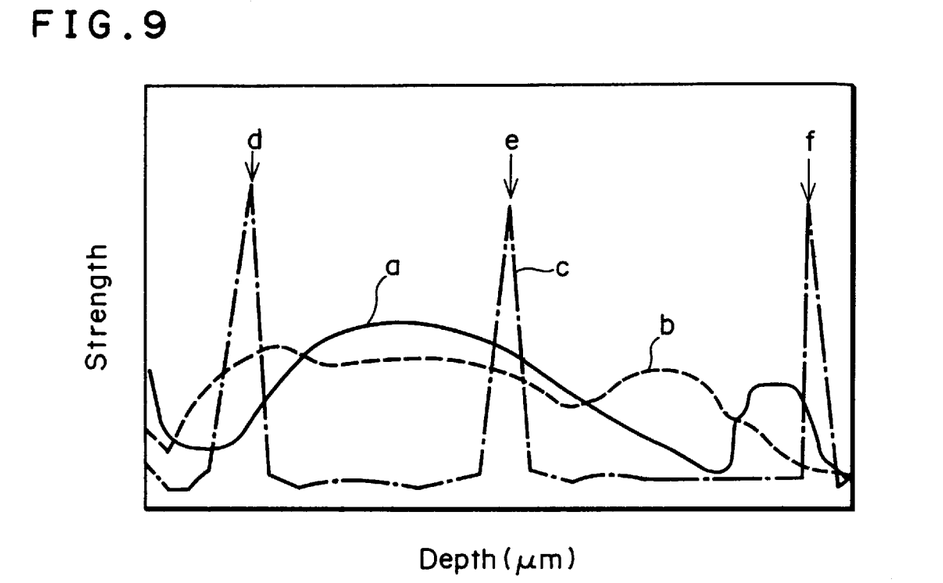
FIG. 9 shows profiles with marker layers.

FIG. 9 presents a graph illustrating profiles obtained when the marker layers 24a to 24c are formed. The horizontal axis of the graph in the figure represents the depth relative to the surface 12a (in units of micrometers) and the vertical axis of the graph in the figure represents the strength of the detected secondary ions 20. The curves "a" and "b" in the graph schematically illustrate the profiles of C and F respectively, i.e., the compositional distribution. In addition, the curve "c" in the graph represents the profile of the element, such as P or As, which constitutes the marker layers 24a to 24c.

The curve "c" has three peaks "d", "e" and "f" in this order over the depth-wise direction. The peak "d" located at the shallowest position represents the strength of the secondary ions generated from the first marker layer 24a, the peak "e" located at the next shallowest position represents the strength of the secondary ions generated from the second marker layer 24b and the peak "f" located at the deepest position represents the strength of the secondary ions generated from the third marker layer 24c.

The peaks "d", "e" and "f" corresponding to the individual marker layers 24a to 24c are detected at specific depth-wise positions in this manner. Since the depth-wise positions at which the marker layers 24a to 24c are formed can be ascertained based upon the film thicknesses of the first insulating film 12c and the second insulating film 12d, calibration related to the depths of the profile "a" of C and the profile "b" of F can be implemented by detecting the depth-wise positions at which the peaks "d", "e" and "f" are located.

As has been explained in reference to the first embodiment, the depth-wise position of the deposited film 16 where the primary ions 18 enter and the position of the surface 12a of the insulating film 12b (12) where the primary ions 18 enter are separated by the distance delta. Because of this, it may not always be clear which depth-wise portion of the deposited film 16 the detected secondary ions 20 correspond to. However, in this embodiment, since the secondary ions generated from the marker layers 24a to 24c are detected together with the secondary ions generated at the deposited film 16, the depths at which the secondary ions are generated can be ascertained accurately. Consequently, by using the test piece structure explained in reference to this embodiment, the depth-wise compositional distribution of the deposited film 16 can be detected with an even higher degree of accuracy.

Sixth embodiment

Figure 10:
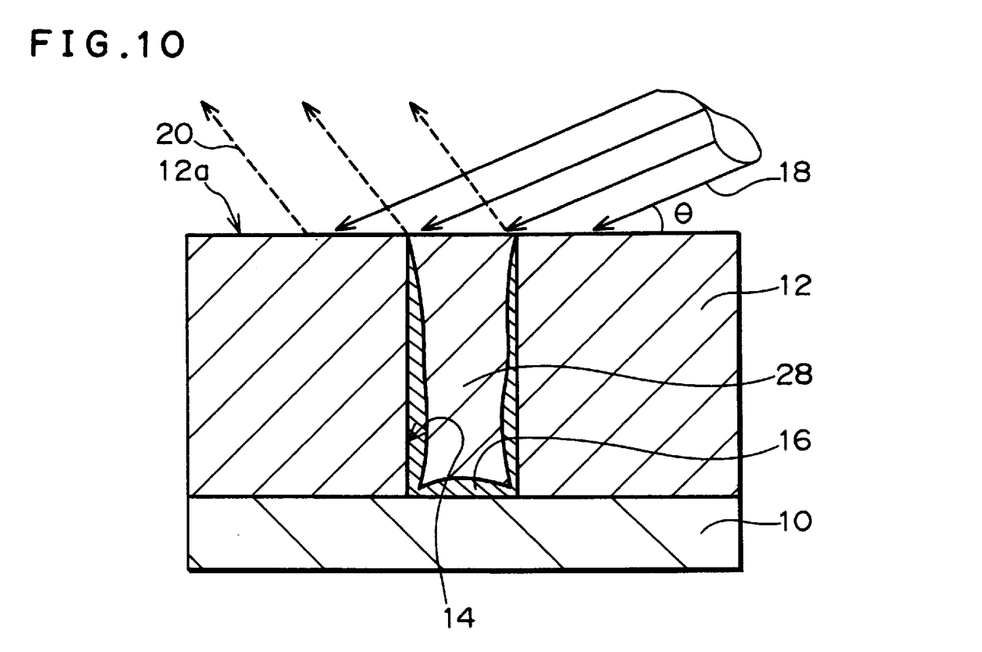
FIG. 10 shows the structure of a test piece in which the inside of the hole is filled.

The sixth embodiment of the present invention is now explained. FIG. 10 shows the structure of a test piece in which the inside of the hole is filled. FIG. 10 illustrates a cross section at a cut-off edge that includes the contact hole 14.

As shown in FIG. 10, in the test piece structure used in this embodiment, the inside of the contact hole 14 is filled with a filling layer 28 constituted of the same material as that constituting the insulating film 12. For instance, if the insulating film 12 is constituted of BPSG, the filling layer 28, too, should be constituted of the same material as the insulating film 12, i.e., BPSG. In addition, the height of the upper surface of the filling layer 28 matches the height of the upper surface of the insulating film 12.

When the filling layer 28 is formed in this manner, the primary ions 18 do not enter deeper inside the hole than beyond the surface 12a of the insulating film 12. Thus, the offset by the distance delta explained earlier is eliminated. In other words, since secondary ions 20 are generated from the portion of the deposited film 16 which is located at the same height as the surface 12a of the insulating film 12 at all times, the compositional distribution of the deposited film 16 over the depth-wise direction can be ascertained accurately and easily.

Seventh embodiment

Now, the seventh embodiment of the present invention is explained. In this embodiment, by adopting the analysis method that has been explained in reference to the individual embodiments above, a pass/fail judgement is made of with respect to the opening of a contact hole. In addition, it will be explained how an improvement in yield can be achieved by incorporating this testing step in the process of manufacturing at semiconductor device.

As explained earlier, when forming a contact hole in an insulating film, a deposited film is accumulated at the side wall of the hole during the etching process. The etching stops due to its selectivity when it reaches the surface of the silicon substrate where the insulating film is formed. In other words, when the surface of the silicon substrate is exposed, the etching does not proceed any further. As a result, the deposited film becomes accumulated over a relatively large thickness at the bottom of the formed contact hole. By checking the presence/absence of the deposited film accumulated at the bottom in this manner, the pass/fail judgement with respect to the opening of a contact hole can be made.

The decision making in regard to the presence/absence of the deposited film can be performed by adopting the method for compositional distribution detection through SIMS described earlier. In other words, by adopting SIMS, the compositional distribution of the deposited film can be detected over the depth-wise direction of the contact hole. If the contact hole is open, a relatively large peak that corresponds to the deposited film accumulated at the bottom emerges in the profile that represents the compositional distribution. If, on the other hand, the contact hole is not open, such a peak does not appear.

Figure 11:
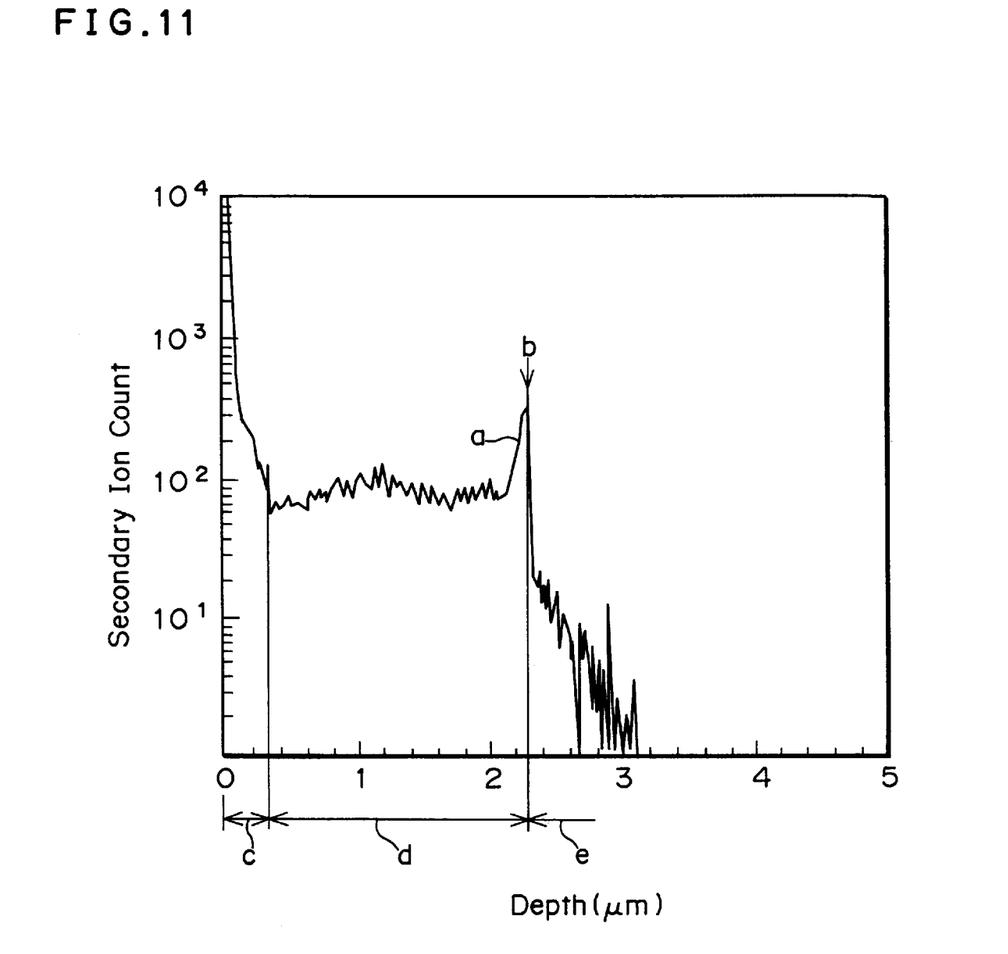
FIG. 11 shows a profile of a good opening.

FIG. 11 presents a graph of profiles obtained when a passed opening is achieved. The test piece structure used in this measurement was constituted by forming an $SiO_2$ film as an insulating film at the upper surface of the silicon substrate and by forming a contact hole in the insulating film. An etching mask constituted of polysilicon was used when forming the contact hole. The horizontal axis of the graph in FIG. 11 represents the depth relative to the surface of the etching mask in units of micrometers with the range from 0 micrometers through 5 micrometers indicated in 0.2 micrometers increments. The vertical axis of the graph in FIG. 11 represents the count of detected secondary ions, with the range from 0 through $10^4$ incremented in logarithmic scale. It is to be noted that the results of the measurement of the profile were obtained using a SIMS apparatus manufactured by Cameca (product name; IMS-3f).

The curve "a" in the graph represents the compositional distribution of F. The area "c" at depths ranging from 0 micrometers through 0.3 micrometers corresponds to the polysilicon constituting the etching mask, and the area "d" at depths ranging from 0.3 micrometers through 2.3 micrometers corresponds to the $SiO_2$ constituting the insulating film. In addition, the area "e" which is deeper than 2.3 micrometers corresponds to the silicon substrate. There is a peak in the curve "a" occurring at the boundary "b" between the area "d" and the area "e." This peak is caused by the element(s) constituting the deposited film accumulated at the bottom of the contact hole. Since the deposited film is accumulated over a larger thickness at the bottom of the contact hole compared to other areas, this appears as a peak in the profile.

Figure 12:
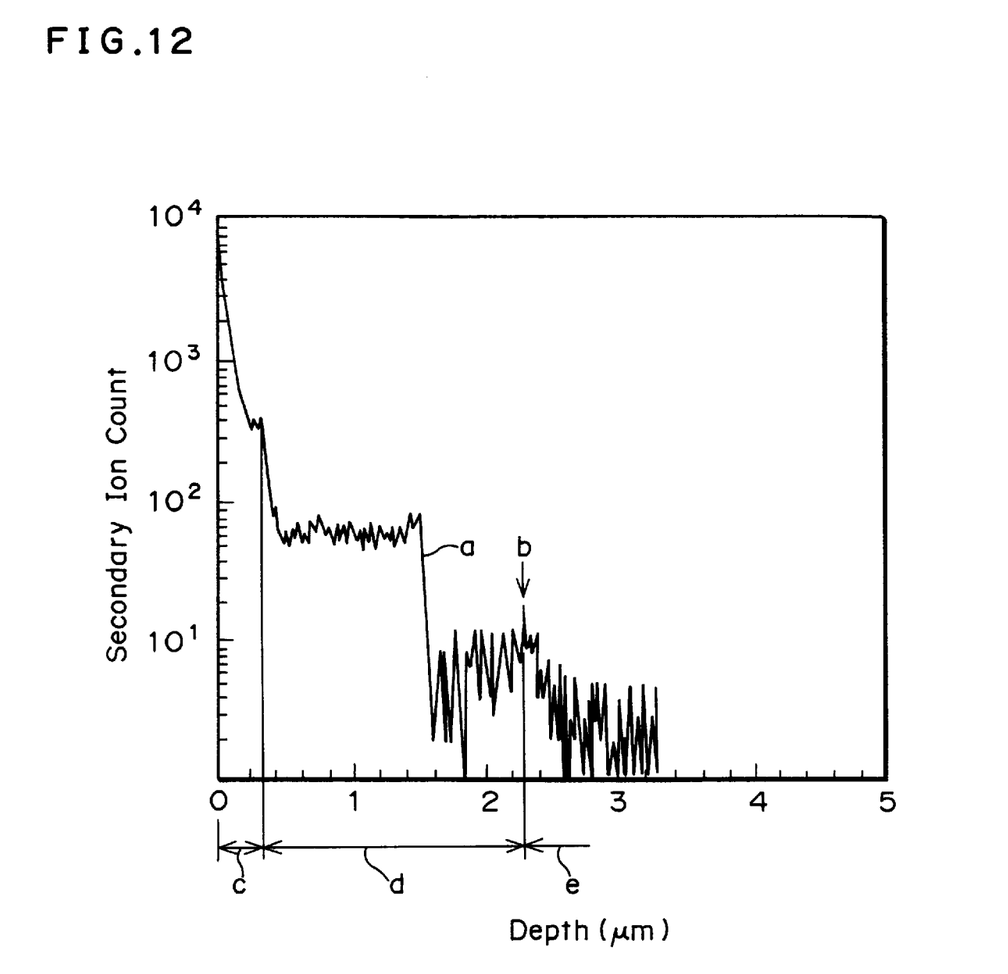
FIG. 12 shows a profile with a defective opening.

FIG. 12, on the other hand, presents a graph of profiles resulting from a failed opening. The results indicated in FIG. 12 were obtained under identical measuring conditions as those employed in the measurement providing the results in FIG. 11. However, in the test piece that was measured, the contact hole was not open completely with the etching having failed to reach the surface of the silicon substrate. In addition, the axes, the increment and the symbols in the figure are identical to those explained in reference to FIG. 11, and their repeated explanation is omitted.

As shown in FIG. 12, the F profile represented by the curve "a" does not have a peak, unlike the profile in FIG. 11. If the contact hole is open properly, there should be a peak occurring at the boundary "b" between the areas "d" and "e". Thus, as is obvious from comparing FIGS. 11 and 12, the pass/fail judgement with respect to the opening of contact holes can be made by adopting the method for compositional distribution detection through SIMS.

Next, incorporation of the testing step described above in the process of manufacturing a semiconductor device is explained. In the process for manufacturing a semiconductor device, a circuit is formed on a wafer. Each of the test piece structures explained in reference to the individual embodiments earlier is formed in a test area on the wafer. For instance, an area that corresponds to one chip of an actual device may be allocated as a test area. After a contact hole is formed on the wafer during the process for manufacturing a given semiconductor device, a testing process for judging pass/fail of the opening of the contact hole is performed following the step for forming the contact hole.

During the testing step to perform the pass/fail judgement with respect to the opening of the contact hole, contact holes formed in the test area described earlier are tested. As has been explained in reference to the second embodiment, an improvement in the detection sensitivity can be achieved by forming a plurality of contact holes in the test area.

Then, the pass/fail judgement with respect to the opening of the contact holes is performed by adopting the method for compositional distribution detection through SIMS. For this purpose, the wafer with the contact holes formed is placed in the analysis chamber of a wafer type SIMS apparatus, which is ideal with its test piece stage and analysis chamber provided in the sizes corresponding to the wafer.

As a result, the test to determine the pass/fail with respect to the opening of contact holes can be performed in-line. If the results of the test indicate that contact holes are not open, the wafer can be returned to the process for contact hole formation, whereas if the holes are open, it can be sent to the next step in the manufacturing process. In addition to the decision making as to the pass/fail with respect to the opening of contact holes, the residue collected in the contact holes can be analyzed at the same time. Thus, a faster, more accurate and less wasteful manufacturing process is achieved compared to the off-line methods adopting SEM and TEM in the prior art.

Eighth embodiment

Now, the eighth embodiment of the present invention is explained. In this embodiment, the pass/fail judgement with respect to the openings of contact holes formed in a wafer through a process for manufacturing a semiconductor device is made by adopting the method for compositional distribution detection through SIMS, as in the seventh embodiment. However, the testing step is implemented independently of the manufacturing process. Namely, in this embodiment, the testing step is not incorporated in the manufacturing process, and the testing step is performed as an off-line method. Consequently, it is not necessary to install the SIMS apparatus for testing in the clean room.

In addition, in this embodiment, the testing is performed by cutting a test area off the wafer. In other words, the test area portion defined on the wafer is cut out and the testing for the pass/fail judgement with respect to the openings is performed on this cut-off portion. This will preclude the necessity for a wafer type SIMS apparatus.

Consequently, this off-line method achieves an advantage in that the facility can be simplified. In addition, as described earlier, the residue accumulated within contact holes can be analyzed at the same time. Thus, this method of testing through SIMS achieves advantages that cannot be achieved in methods adopting SEM and TEM in the prior art.

In the method for compositional distribution detection at a hole internal surface according to the present invention, secondary ions are generated by radiating primary ions into the surface of an insulating film where a contact hole is formed. Then, by performing mass spectrometry on the secondary ions, the compositional distribution of the deposited film formed at the internal surface of the contact hole is detected. With this method, the compositional distribution of the deposited film over the depth-wise direction of the contact hole can be ascertained. Based upon the information thus acquired, various unknown aspects of the phenomena occurring during the etching process can be resolved. In addition, the etching conditions for contact hole formation such as the composition of the etching gas and the various settings at the etching apparatus can be optimized. Consequently, the method can be effectively adopted in the formation of contact holes with a smaller diameter and a greater depth.

The entire disclosure of Japanese Patent Application No. 9-197461 filed on Jul. 23, 1997 including specification, claims, drawings and summary is incorporated herein by reference in its entirety.

What is claimed is:

1. A method for testing a semiconductor device comprising:

generating secondary ions by radiating primary ions into a surface of a test insulating film where contact hole(s) is/are formed, said radiating occurring at a constant oblique angle relative to an upper surface of said test insulating film; and performing mass spectrometry on said secondary ions to detect a depth-wise compositional distribution of said test insulating film and of an internal surface of said contact hole(s).

2. A method for testing a semiconductor device according to claim 1, further comprising:

comparing said depth-wise compositional distribution thus ascertained and a depth-wise compositional distribution of a reference insulating film that has been measured in advance.

3. A method for testing a semiconductor device according to claim 1, further comprising:

verifying whether said contact hole(s) has/have been formed in the test insulating film or not.

4. A method for testing a semiconductor device according to claim 1, further comprising:

determining said depth-wise distribution of said composition of said test insulating film as a depth-wise compositional distribution of foreign matter adhering to said internal surface of said contact hole.

5. A method for testing a semiconductor device according to claim 1, wherein:

inside of said contact hole is filled with a material identical to that constituting said test insulating material.

6. A method for testing a semiconductor device according to claim 1, further comprising:

providing at least one marker layer in advance at a specific depth-wise position relative to said surface of said insulating film where said contact hole is formed.

7. A method for testing a semiconductor device according to claim 6, wherein said providing at least one marker layer comprises:

providing a first marker layer at a bottom surface of said insulating film;

providing a second marker layer at an intermediate position of said insulating film; and providing a third marker layer at an upper surface of said insulating film.

8. A method for testing a semiconductor device according to claim 1, wherein said radiating primary ions comprises:

scanning said primary ions in the surface of the test insulating film in the form of a ion beam.

9. A method for testing a semiconductor according to claim 1, wherein:

an angle of incidence of the primary ions ranges from 7 degree to 70 degree.

10. A method for testing a semiconductor according to claim 1, wherein:

an angle of incidence of the primary ions ranges from 7 degree to 30 degree.

11. A method for testing a semiconductor according to claim 1, wherein:

there is a plurality of contact holes in the area to be tested.

12. A method for testing a semiconductor device according to claim 11, wherein said plurality of contact holes are of varying diameters.

13. A method for testing a semiconductor according to claim 1 wherein:

said primary ions are oxygen ions.

14. A method for testing a semiconductor according to claim 1, wherein:

said test insulating film do not include component of the foreign matter adhering to said internal surface of said contact hole.

15. A method for testing a semiconductor device according to claim 1, wherein said radiating by said primary ions includes sputter etching said test film.

16. A method for testing a semiconductor device according to claim 1, wherein said radiating by said primary ions gradually reduces a height of said upper surface of said test film, allowing scanning of said primary ions down the contact hole.

17. A method for testing a semiconductor device according to claim 16, wherein said scanning down an entire length of said contact hole.

18. A method for testing a semiconductor device according to claim 1, further comprising, before said generating, cutting a test area from a wafer including the semiconductor device.

19. A method for testing a semiconductor device comprising:

radiating primary ions into a surface of a test insulating film where contact hole(s) is/are formed from a constant oblique to generate secondary ions;

performing mass spectrometry on said secondary ions to detect a depth-wise compositional distribution of said test insulating film; and determining said depth-wise distribution of said composition of said test insulating film as a depth-wise compositional distribution of foreign matter adhering to said internal surface of said contact hole.

20. A method for testing a semiconductor device comprising:

radiating primary ions into a surface of a test insulating film where contact hole(s) is/are formed from a constant oblique to generate secondary ions; and performing mass spectrometry on said secondary ions to detect a depth-wise compositional distribution of said test insulating film, wherein said test insulating film does not include component of foreign matter adhering to an internal surface of said contact hole.

* * * * *